(12) United States Patent
Meyer

(10) Patent No.: US 7,049,107 B1
(45) Date of Patent: *May 23, 2006

(54) METHOD OF PRODUCING PHOSPHATIDYLSERINE

(75) Inventor: Randal Meyer, Sioux Center, IA (US)

(73) Assignee: Sioux Biochemical, Inc., Sioux Center, IA (US)

( * ) Notice: Subject to any disclaimer, the term of this patent is extended or adjusted under 35 U.S.C. 154(b) by 232 days.

This patent is subject to a terminal disclaimer.

(21) Appl. No.: 10/670,006

(22) Filed: Sep. 24, 2003

Related U.S. Application Data

(63) Continuation-in-part of application No. 10/424,517, filed on Apr. 28, 2003, now Pat. No. 6,878,532.

(51) Int. Cl.
*C12P 13/04* (2006.01)
*C12P 7/64* (2006.01)
*C12N 1/20* (2006.01)

(52) U.S. Cl. ............. 435/106; 435/117; 435/128; 435/129; 435/131; 435/132; 435/194; 435/253.5

(58) Field of Classification Search ............ 435/106, 435/117, 128, 129, 131, 132, 194, 253.5
See application file for complete search history.

(56) References Cited

U.S. PATENT DOCUMENTS

| | | | |
|---|---|---|---|
| 3,681,412 A | 8/1972 | Betzing et al. | |
| 4,496,489 A | 1/1985 | Sengupta | |
| 4,595,680 A | 6/1986 | Valle et al. | |
| 4,624,919 A | 11/1986 | Kokusho et al. | |
| 4,714,571 A | 12/1987 | Tremblay et al. | |
| 4,783,402 A | 11/1988 | Kokusho et al. | |
| 4,861,521 A | 8/1989 | Suzuki et al. | |
| 5,100,787 A | 3/1992 | Shimizu et al. | |
| 5,155,099 A | 10/1992 | Brachwitz et al. | |
| 5,315,023 A | 5/1994 | De Ferra et al. | |
| 5,466,841 A | 11/1995 | Horrobin et al. | |
| 5,700,668 A | 12/1997 | Ferra et al. | |
| 5,856,196 A | 1/1999 | Alvarez et al. | |
| 5,900,409 A | 5/1999 | Sakai et al. | |
| 5,965,413 A | 10/1999 | Sakai et al. | |
| 5,972,380 A | 10/1999 | Dalake et al. | |
| 6,117,853 A | 9/2000 | Sakai et al. | |
| 6,426,423 B1 | 7/2002 | Copeland et al. | |
| 6,635,456 B1 * | 10/2003 | Kirschner et al. | 435/134 |
| 6,660,504 B1 * | 12/2003 | Yamane et al. | 435/106 |
| 6,878,532 B1 * | 4/2005 | Meyer | 435/106 |
| 2002/0072508 A1 | 6/2002 | Rutenberg | |

FOREIGN PATENT DOCUMENTS

| | | |
|---|---|---|
| EP | 0 727 491 A1 | 8/1996 |
| EP | 1 048 738 A1 | 11/2000 |
| EP | 1 213 294 A1 | 6/2002 |
| WO | WO 00/18945 | 4/2000 |
| WO | WO 00/77183 A1 | 12/2000 |

* cited by examiner

*Primary Examiner*—Herbert J. Lilling
(74) *Attorney, Agent, or Firm*—McKee, Voorhees & Sease, P.L.C.

(57) ABSTRACT

A novel method of producing PS is described herein. The method first involves producing PLD enzyme through the use of enzyme-producing microorganisms. The PLD enzyme is reacted with a lecithin and source of serine to produce the phosphatidylserine (PS). The method differs from prior methods in several ways. First, it incorporates a novel strain of PLD enzyme-producing organism in a preferred embodiment. It is also the first known PS production method that allows for the reuse of the enzyme and serine components to enhance efficiency and productivity. It further incorporates a novel solvent system, unique stabilization agents for the PLD enzyme, as well as optimized reaction conditions.

7 Claims, No Drawings

METHOD OF PRODUCING PHOSPHATIDYLSERINE

CROSS-REFERENCE TO RELATED APPLICATIONS

This application is a continuation-in-part of U.S. patent application Ser. No. 10/424,517 filed on Apr. 28, 2003 now U.S. Pat. No. 6,878,532.

FIELD OF THE INVENTION

This invention relates to a novel and efficient method of producing phosphatidylserine.

BACKGROUND OF THE INVENTION

Phosphatidylserine, or PS, is a naturally occurring phospholipid nutrient. PS is essential to the functioning of all of the cells of the body, but is most concentrated in the brain. PS is embedded in cell membranes and, along with other phospholipids, makes up the basic structural components of the cell membrane. These membrane phospholipids play an important role in cell-to-cell communication and transfer of biochemical messages into the cell, which trigger cellular responses. PS is essential to the healthy functioning of the human brain where it affects an assortment of nerve cell functions.

The consistent clinical findings on PS indicate that by working in nerve cell membranes, PS helps optimize a variety of functions indispensable at the level of the single nerve cell. These encompass homeostatic (basis, survival-type) processes, maintenance (renewal, repair, "housekeeping"), and specialized processes unique to the nerve cell. Studies have also shown that supplemental PS may indirectly improve cognitive function by improving the health of individual nerve cells. PS has also shown promise in improving cognitive function in patients with Alzheimer's disease and/or dementia.

PS and the other phospholipids (PL) are large molecules that hold together the cell's membranes. The PL pack together side-to-side, in a two-layer molecular structure, creating a membrane matrix into which proteins and other membrane constituents are inserted and secured. The PS phospholipids are one of six phospholipid classes, the others being phosphatidic acid (PA), phosphatidyl-cholines (PC), -ethanolamines (PE), and inositols (PI); and the sphingomyelins.

Until recently, supplemental PS was available only from animal sources, such as bovine brain. However, dietary consumption of bovine brain has raised concerns, primarily due to the "mad cow" disease epidemic in Great Britain. Phosphatidylserine derived from alternative sources has therefore become the predominant form of PS supplements in the industry.

Typical methods for preparing PS involve reacting phosphatides with serine in the presence of phospholipase D enzyme (PLD). PLD used in the reaction is normally produced from centrifuged fermentation broths of microorganism strains capable of producing extracellular PLD. The present inventor has now discovered a unique method of producing PS that has improved upon these previous aspects of PS production.

Accordingly, it is a primary objective of the present invention to provide a novel method and means of producing phosphatidylserine (PS) that is more efficient than previous PS production methods.

It is a further objective of the present invention to provide a novel method and means of producing PS that provides enhanced transphosphatidylation activity in comparison to previous methods.

It is a further objective of the present invention to provide a novel method and means of producing PS that provides enhanced enzymatic stability.

It is still a further objective of the present invention to provide a novel method and means of producing PS that uses an optimized production growth media and contains no animal-origin components.

It is yet a further objective of the present invention to provide a novel method and means of producing PS that reuses enzyme and serine components in the phosphatidylserine production reaction.

It is a further objective of the present invention to provide a novel method and means of reclaiming the unused serine from the phosphatidylserine production reaction.

It is a further objective of the present invention to provide a novel method and means of producing PS that uses a unique strain of organism for the manufacture of phospholipase D enzyme.

The method and means of accomplishing each of the above objectives as well as others will become apparent from the detailed description of the invention which follows hereafter.

SUMMARY OF THE INVENTION

The present invention describes a method of producing phosphatidylserine (PS) that has several unique aspects. The method is more efficient and provides better transphosphatidylation activity in comparison to previous PS production methods.

The method first involves producing phospholipase D (PLD) enzyme from phospholipase-producing microorganisms. The PLD is produced in an optimized growth media that preferably includes *Streptomyces cinnamoneum*, and most preferably includes ATCC 11874. The enzyme is then harvested, filtered, and concentrated, and preferably stabilized through the use of a chelating agent.

The PLD is next reacted with a lecithin and racemic or enantiomerically pure serine, preferably L-serine, and a lower ($C_1$–$C_5$) alcohol to produce PS. To accomplish this, the phosphatide is dissolved in one or more organic solvents. Serine, a metal, and buffer that is preferably 20–50 mM sodium acetate are added to the PLD. The organic and aqueous phases are combined, a lower alcohol ($C_1$–$C_5$) is added to create the aqueous/organic interphase wherein the transphosphatidylation reaction occurs, and the diphasic mixture is then reacted, preferably with rapid stirring, and at a preferred temperature and time of 32±1° C. and for 184 hours, respectively.

The present invention differs from previous methods in that it incorporates a chelating agent and calcium or other metal to selectively enhance the transphosphatidylation activity of PLD. Further, the present method is the first to use a combination of organic solvent and a lower ($C_1$–$C_5$) alcohol during the transphosphatidylation reaction in order to create an appropriate aqueous and organic interphase and maximize PS production. In addition, the method is the first known to reuse the PLD enzyme and serine up to five times in the production reaction, thereby increasing the efficiency of PS production. The method is also the first known to reclaim the serine using an ethanol fractionation of the serine. A preferred embodiment of the invention further incorporates a previously unknown strain of *Streptomyces*

*cinnamoneum* in the production of phospholipase D, resulting in improved growth and enzyme characteristics.

DETAILED DESCRIPTION OF THE PREFERRED EMBODIMENT

The present invention relates to the development of an improved method of manufacturing phosphatidylserine (PS) using phospholipase D (PLD) enzyme derived from microorganisms. According to the invention, phospholipid is reacted with serine in the presence of PLD enzyme to produce PS.

The PLD enzyme used in the invention is one that is produced by a PLD enzyme-producing microorganism. The invention is intended to encompass use of any PLD enzyme-producing microorganism, specific examples of which include those belonging to the genus *Nocardiopsis*, such as *Nocardiopsis* sp. No. 779 (FERM-P No. 6133; international deposit number BP 512 under the Budapest Treaty), those belonging to the genus *Actinomadura*, such as *Actinomadura* sp. No. 362 (FERM-P No. 6132; international deposit number BP 511 under the Budapest Treaty), those belonging to the genus *Kitasatosporia*, such as *Kitasatosporia chromogena*; those belonging to the genus *Micromonospora*, such as *Micromonospora chalcea*; and those belonging to the genus *Streptomyces*, such as *Streptomyces* sp. ATCC strain #55717 (see U.S. Pat. No. 5,700,668), with *Streptomyces cinnamoneum* being preferred.

The present inventor has also discovered a novel strain of *Streptomyces cinnamoneum* that is especially advantageous for use in this invention. This strain provides the unique advantages of allowing higher extracellular production of phospholipase D and a considerably higher ratio of transphosphatidylation to hydrolytic activity of the PLD enzyme, relative to the IFO 12852 Streptomyces cinnamoneum strain. The strain also provides advantageous cultural characteristics that are useful in industrial-scale fermentation. Specifically, the new strain has a large fermentative colony morphology that enables simpler removal from the spent culture media following fermentation. This strain also provides better utilization of the fermentation media, with fewer undesirable by-products. It has been deposited in the American Type Culture Collection, 12301 Parklawn Drive, Rockville, Md. 20852 USA as ATCC PTA-6205, and is specifically incorporated herein by reference. Said *Streptomyces cinnamoneum* 11874 was deposited on Sep. 13, 2004.

Previously used PLD enzyme production methods have incorporated IFO 12852, which has comparatively lower extracellular production of PLD and a higher ratio of hydrolytic to transphosphatidylation activity. The small fermentative cell morphology creates downstream processing challenges. Fermentative growth of this organism also creates more undesirable by-products in comparison to the preferred *Streptomyces cinnamoneum* strain of this invention.

The PLD enzyme-producing microorganism is grown on an appropriate growth media capable of enabling good growth of the organism and enabling production of PLD enzyme. Appropriate broth-based growth medias for this purpose are well known in the art and include, but are not limited to glucose-asparagine, glycerol-asparagine, yeast-malt media, starch-inorganic salt medium, sucrose-nitrate, nutrient liquid culture media, tyrosine, peptone-yeast-iron, and oatmeal media. Depending on the type of microorganism used, the type of media preferred for this purpose will vary. For instance, preferred fermentation media for *Streptomyces* include broth-based media containing at least glucose and yeast extract.

The media may also include various carbon, nitrogen, inorganic salts, and/or trace nutrients. Examples of appropriate carbon sources include glucose, fructose, sucrose, lactose, starch, glycerol, dextrin, molasses, sorbitol, fatty acids, oils and fats, crude lecithin, alcohols and organic acids. The nitrogen sources may be inorganic or organic. Examples of inorganic nitrogen sources include ammonium nitrate, ammonium sulfate, urea, sodium nitrate, ammonium phosphate monobasic, ammonium phosphate dibasic and ammonium chloride. Examples of organic nitrogen sources include flours, brans and oil extraction residues of soybean, rice, corn, cotton seed, rape seed and wheat, corn steep liquor, peptone, yeast extract, meat extract, casein and amino acids. Examples of inorganic salts and trace nutrients include salts of phosphoric acid, magnesium, potassium, iron, aluminum, calcium, manganese and zinc, vitamins, nonionic surface-active agents and defoamers. Such substances promote the growth of the microorganisms or the production of phospholipase DM, and may be used as required.

A preferred growth media for use with *Streptomyces* incorporates yeast extract, malt extract, glucose, and peptone. In this regard, the yeast extract and malt extract provide a source of vitamins, nitrogen, amino acids, and complex carbohydrates for the bacteria. The glucose provides an easily utilizable source of carbon. Peptone provides a source of nitrogen and amino acids. A preferred brand of peptone is Select Soytone (BD Biosciences, Sparks, Md.) because it is plant-based and contains no animal proteins.

A most preferred growth media includes potassium phosphate ($KH_2PO_4$) and magnesium sulfate ($MgSO_4$) to provide essential minerals for bacterial growth, as well as an antifoam agent to control foaming during the fermentation process. Appropriate antifoaming agents for this purpose are well known in the art.

The organisms are grown for a time period sufficient to yield a packed cell volume of 100–150 µL/mL, yielding a PLD enzyme activity of about 10–15 U/mL according to the assay method of Artiss et al. (Microchemical Journal, 1980, 25, 153–168). This time period will generally range from about 15–20 hours. The organisms should be grown at ambient temperatures, with about 25–35° C. being preferred.

The culture is centrifuged and/or filtered to yield a culture supernatant which is then concentrated and diafiltered, preferably through the use of a 10 kD MWCO membrane, to remove small media components and salts. A chelating agent is then added to the culture supernatant to bind residual metals and increase the transphosphatidylation activity for producing PS during the reaction step. Chelating agents are well known in the art and include, but are not limited to, EDTA, EGTA, EDDA, citric acid, iminodiacetic acid, and nitriloacetic acid. EDTA is preferred for this purpose. The pH of the media is then adjusted to a pH of 5–8, with a pH of 6–7 being preferred for stability reasons, and is stored at 2–8° C. The culture supernatant may be used as-is, or purified utilizing methods known in the art.

The next step of the invention is to prepare the PS by reacting the PLD enzyme produced in the previous steps with a source of serine and a source of lecithin or other phosphatidylcholine-containing phospholipid as a substrate. Any lecithin is appropriate for use in the invention, including lecithin derived from natural sources (i.e. soy, egg, etc.) or synthetic sources, and may include high purity lecithin, such as Epikuron® 200 (Lucas Meyer), as well as low-cost, low purity lecithins. The lecithin is first dissolved in an organic solvent. Any organic solvent capable of dissolving the lecithin is suitable for this purpose. Examples of appropriate organic solvents include, but are not limited to heptane, hexane, toluene, ethyl acetate, diethyl ether, petroleum ether, chloroform, dichloromethane, and benzene.

Simultaneously to or at a different time than the above-referenced step, a source of serine and a buffer such as HEPES, TRIS-hydrochloride, TRIS-acetate, BIS-TRIS, sodium citrate, potassium acetate, sodium acetate, sodium-phosphate, potassium phosphate, and potassium acetate, are dissolved in the concentrated PLD enzyme prepared above. Sodium acetate is the preferred buffer for this purpose due to its pH buffering range and since it is relatively inexpensive. Any source of serine may be used in this step, including racemic or enantiomerically pure serine, with L-serine being preferred. Calcium chloride ($CaCl_2$), or other metal salt such as barium, manganese, magnesium, zinc, and/or aluminum chloride, sulfate, etc. is then preferably added to the solution in order to further enhance the transphosphatidylation activity of the PLD enzyme.

The lecithin solution is then combined with the serine solution and agitated to mix. With continued agitation, one or more $C_1$–$C_5$ lower alcohols, such as methanol, ethanol, isopropanol, butanol, pentanol, etc., is added in order to create an aqueous/organic interphase wherein the lecithin transphosphatidylation reaction occurs. The alcohol is added in a ratio of 0.1–1 volume alcohol per volume of organic solvent. The pH of the reaction mixture is adjusted to between about 5–8, with about 5.6–6.0 being preferred for optimum enzyme activity. The mixture is allowed to react for 18±4 hours at a temperature range of 22–45° C., preferably with agitation and/or rapid stirring.

Once the reaction is complete, the reaction mixture is allowed to separate into two phases by unit gravity or centrifugation. The organic phase containing PS separates to the top and is removed, leaving the aqueous phase containing serine, enzyme, buffer and alcohol remaining on the bottom.

In a preferred embodiment, the method includes a recycling step wherein PLD enzyme and serine are reused for better efficiency. In this step, fresh lecithin is dissolved in hexane or other organic solvent and transferred to the reaction vessel. The aqueous phase is then transferred back into the reactor and reincubated, thereby reusing the same enzyme and serine. This process may be repeated up to a total of 5 times using the same serine/enzyme solution with fresh lecithin dissolved in organic solvent.

Once the serine/enzyme solution has been used for the last time in the reaction, the aqueous phase solution is stored at 2–8° C. for 24–72 hours to allow any residual phospholipids to crystallize. The solution is next filtered to remove residual phosphatidylserine, then diafiltered, preferably through a 10 kD MWCO membrane to separate the enzyme (retentate) from the serine (permeate). The serine permeate is then precipitated with a lower alcohol ($C_1$–$C_5$) which is preferably ethanol to selectively separate the serine from the contaminants, including the choline. The serine precipitate is then recovered and dried, yielding serine which may be reused in the reaction, yielding results comparative to that of fresh serine. The concentrator retentate containing the enzyme can also be reused directly or following purification by ion exchange chromatography.

The phosphatidylserine contained in the organic phase previously described is precipitated from organic solvent with a lower alcohol or ketone ($C_1$–$C_5$), and preferably acetone, and the material is dried using conventional means, including heated, forced air dryer or vacuum dryer. Preferably, antioxidants are added to the serine prior to drying. Following drying, the PS is ground and packaged. The purity level may be measured by chromatography or other means.

In addition to the methods already described, the PLD enzyme produced in accordance with this invention may be used for any other purposes known in the art for PLD enzyme, as well as any possible future purposes. For instance, PLD is used for exchanging a base of a phospholipid, utilizing primary, secondary or aromatic alcohols in the preparation of phosphatidyl-alcohol compounds. This involves incubating a base of a phospholipid, such as lecithin, as a starting material, with a hydroxyl-containing receptor, in the presence of phospholipid D in a suitable solvent/alcohol mixture, as already described above for the dissolution of lecithin, under the same types of conditions already described above. Using PLD for these alternate purposes offers the same advantages described for the improved enzyme of this invention.

The proposed mechanism of the transphosphatidylation reaction is as follows (using phosphatidylcholine as a sample phosphlipid) (Yang et al., J. Biol. Chem., 242:3, 477):

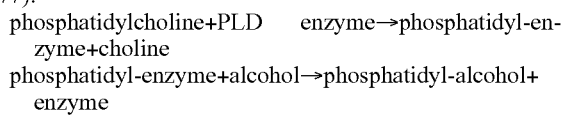

phosphatidylcholine+PLD enzyme→phosphatidyl-enzyme+choline phosphatidyl-enzyme+alcohol→phosphatidyl-alcohol+enzyme The method of the present invention differs from prior art PS production methods in several ways. First, the present method utilizes a unique strain of PLD enzyme-producing organism, namely *Streptomyces cinnamoneum* ATCC. This organism provides superior results in terms of growth and enzyme characteristics. The new method uses an optimized production growth media and contains no animal-origin components.

A preferred embodiment of the invention incorporates EDTA or other chelating agent and $CaCl_2$ or other metal to selectively enhance the transphosphatidylation activity of the PLD enzyme. The new method also incorporates a preferred embodiment that utilizes an organic phase combination of 2 unique solvents: hexane (or heptane) and isopropanol, preferentially in a 2:1 ratio of hexane/isopropanol. This particular combination of solvents has been found to provide optimum transphosphatidylation activity, thus producing highest PS yields.

The method of this invention further incorporates a preferred embodiment that includes a different pH optimum of 5.6–6.0 which provides optimum enzyme activity, yielding the highest amount of PS, as well as an optimum temperature of 32±1° C. which provides continued enzyme stability over the course of four-five subsequent reactions that utilize the same enzyme. Further, the present PS production method separates the organic phase containing the PS from the aqueous solution via decantation and centrifugation, rather than via a more complex filtration method.

In addition, the present invention utilizes repeated incubations of the same enzyme/serine/buffer solution, making the PS production method more efficient and less expensive. Furthermore, the non-utilized serine may be reclaimed from the reaction mixture by separating the enzyme from the serine via diafiltration followed by precipitation of the permeate (serine) with an alcohol. This serves to separate the serine from most other contaminants, including the by-product choline, which remains soluble in the alcohol. This is in contrast to previous methods that incorporate electrodialysis as a means for reclaiming unused serine.

The following example is provided to further illustrate the invention. It is not intended to limit the invention in any manner.

EXAMPLE 1

Preferred Method of Producing Phosphatidylserine

1) Streptomyces cinnamoneum is grown in a 250 L fermenter utilizing growth media consisting of yeast extract (4 g/L), glucose (4 g/L), malt extract (10 g/L), Select Soytone peptone (5 g/L), $KH_2PO_4$ (10 mM), $MgSO_4$ (1 g/L), and antifoam (SAG 5693, 0.2 mL/L) for 15–20 hours at 30±2° C., with sparging, yielding a packed cell volume of 100–150 µL/mL and producing a PLD enzyme activity of about 10–15 U/mL according to the assay method of Artiss et al. (Microchemical Journal, 1980, 25, 153–168).

2) The media is harvested by centrifugation.

3) Cellular debris is removed from the centrifuged media by filtration through a filter press equipped with 0.2 micron (nominal) filter pads.

4) The PLD enzyme-containing media is concentrated approximately 5 times (~40 L) through a 10 kD molecular weight cut-off (MWCO) membrane and exchanged with water to remove most of the small media components and salts.

5) Following the concentration/exchange process, 10–15 mM EDTA is added to the enzyme for stabilization purposes and to increase transphosphatidylation activity for producing phosphatidylserine (PS). The media is adjusted to pH 6.5, sterile filtered, and stored at 2–8° C. until used in the reaction.

6) The reaction is then performed in a reactor tank utilizing the following conditions:
   a. 5 kg of PC-enriched lecithin (Centrolex® FP-40; Central Soya) is dissolved in 13.3 L hexane or heptane;
   b. 7 kg of L-serine and 984 g of sodium acetate and 360 g of sodium chloride are dissolved in 40 L concentrated PLD enzyme. Calcium chloride (2 L of 2.5 M solution) is then added to the solution and the pH of the solution is adjusted to 5.8±0.2;
   c. The two solutions are combined in the reactor tank. 6.6 L of isopropanol is added to the reaction mixture and the pH readjusted to 5.8±0.2;
   d. The reaction is allowed to proceed for 18±4 hours at 32±1° C. with rapid stirring.

7) a. The agitation is stopped and the reaction mixture is allowed to separate into 2 phases. The majority of the aqueous phase, containing serine, sodium acetate, NaCl, enzyme and alcohol separates to the bottom and can be drawn off;
   b. The top phase (organic phase containing PS) is removed from the tank. It is allowed to separate from any residual aqueous phase or interphase by unit gravity or centrifugation;
   c. Fresh lecithin is dissolved in hexane or heptane and transferred to the reactor tank. The aqueous material is then transferred back into the reactor tank and reincubated, thereby reusing the same enzyme and serine for better efficiency. This process is repeated up to a total of 5 incubations with the same enzyme/serine solution;
   d. The PS solution is precipitated using 4 volumes of acetone to recover the PS.

8) The precipitated PS is filtered from the acetone and antioxidants are added prior to drying the material in a dryer oven.

9) Following drying, the PS is ground using a mill and purity level is determined via HPLC.

10) The ground PS material is blended to the proper purity level.

11) After blending, the PS material is packaged in drums.

12) After the aqueous serine/enzyme solution is used for the last time in the reaction, the solution is filtered and then run through a concentrator with a 10 kD membrane to separate the enzyme (retentate) from the serine (permeate).

13) The serine permeate is then precipitated with 4 volumes of ethanol to selectively precipitate serine from the contaminants, including the choline.

14) The serine precipitate is then recovered utilizing the filter press.

15) The wet serine filter cake is dried in a dryer oven yielding serine which then can be reused in the reaction, yielding results similar to that of new serine.

16) The concentrator retentate containing the enzyme can also be reused directly or purified by ion exchange chromatography and reused in the reaction.

EXAMPLE 2

Preferred Method of Producing Phosphatidylserine

1) *Streptomyces cinnamoneum* is grown in a fermenter utilizing growth media consisting of yeast extract (4 g/L), glucose (4 g/L), malt extract (10 g/L), Select Soytone peptone (5 g/L), $KH_2PO_4$ (10 mM), $MgSO_4$ (1 g/L), and antifoam (SAG 5693, 0.2 mL/L) for 15–20 hours at 30±2° C., with sparging, yielding a packed cell volume of 100–150 µL/mL and producing a PLD enzyme activity of about 10–15 U/mL according to the assay method of Artiss et al. (Microchemical Journal, 1980, 25, 153–168).

2) The media is harvested by centrifugation.

3) Cellular debris is removed from the centrifuged media by filtration through a filter press equipped with a 0.2 micron (nominal) filter pad.

4) The PLD enzyme-containing media is concentrated approximately 5 times (~40 L) through a 10 kD molecular weight cut-off (MWCO) membrane to remove a substantial amount of low molecular weight contaminants. The material is not exchanged with water.

5) Following the concentration process, the media is precipitated with 2 volumes of acetone. After standing at 2–8° C. for 24–48 hours the majority of the clear acetone supernatant is decanted off and discarded.

6) The residual acetone slurry is centrifuged at approximately 2500×g to separate the precipitated phospholipase D enzyme from the acetone supernatant.

7) The enzyme precipitate is then dissolved in 20–40 L of 10 mM sodium acetate buffer, pH 6.5.

8) The enzyme solution is made 10–15 mM EDTA, pH adjusted to 6.5, sterile filtered and stored at 2–8° C. until used in the transphosphatidylation reaction.

9) The transphosphatidylation reaction is performed as described in steps 6)–16) of Example 1.

It should be appreciated that minor modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A method of exchanging a base of a phospholipid comprising:

producing phospholipase D (PLD)) enzyme from phospholipase-producing microorganisms selected from the genus *Streptomyces*: combining the PLD enzyme with a hydroxyl-containing compound and a phospholipid to form a reaction mixture;

said phospholipid being dissolved in an organic solvent;

adding an alcohol to the reaction mixture to create an aqueous/organic interphase;

allowing the mixture to react for a time period sufficient to exchange the base;

allowing the reaction mixture to separate into an aqueous phase and an organic phase following the exchange of the base;

incubating the aqueous phase with phospholipid; separating the PLD enzyme from unreacted hydroxyl-containing compound; and reusing the separated hydroxyl-containing compound and the separated PLD enzyme in the combination step.

2. The method of claim 1 whereby the aqueous phase is incubated with phospholipid that is different from the phospholipid used in the combining step.

3. The method of claim 1 further including the steps of: centrifuging the PLD enzyme following the production step to produce a culture supernatant; and adding a chelating agent to the culture supernatant.

4. The method of claim 3 whereby the chelating agent is EDTA.

5. The method of claim 4 wherein the reaction mixture is agitated or stirred during the combination and reacting steps.

6. A method of exchanging a base of a phospholipid comprising:

combining a phospholipid with a hydroxyl-containing compound in the presence of phospholipase D (PLD) enzyme to produce a phosphatidyl-enzyme product, whereby the PLD enzyme is produced from phospholipase-producing microorganisms *Streptomyces cinnamoneum* ATCC strain # PTA-6205.

7. A method of exchanging a base of a phospholipids comprising:

producing phospholipase D (PLD) enzyme from phospholipids-producing microorganisms; combining the PLD enzyme with a hydroxyl-containing compound and a phospholipid to form a reaction mixture; said phospholipid being dissolved in an organic solvent;

adding an alcohol to the reaction mixture to create an aqueous/organic interphase; and allowing the mixture to react for a time period sufficient to exchange the base; wherein the phospholipid-producing microorganisms are *Streptomyces cinnamoneum* ATCC strain #PTA-6205.

* * * * *